United States Patent
Yang et al.

(10) Patent No.: US 10,898,577 B2
(45) Date of Patent: Jan. 26, 2021

(54) CONJUGATE OF GINSENOSIDE COMPOUND K AND GLYCOL CHITOSAN AND AN ANTI-TUMOR USE THEREOF

(71) Applicant: UNIVERSITY-INDUSTRY COOPERATION GROUP OF KYUNGHEE UNIVERSITY, Gyeonggi-do (KR)

(72) Inventors: Deok Chun Yang, Gyeonggi-do (KR); Yeon Ju Kim, Gyeonggi-do (KR); Mathiyalagan Ramya, Gyeonggi-do (KR)

(73) Assignee: UNIVERSITY-INDUSTRY COOPERATION GROUP OF KYUNG HEE UNIVERSITY, Gyeonggi-Do (KR)

( * ) Notice: Subject to any disclaimer, the term of this patent is extended or adjusted under 35 U.S.C. 154(b) by 0 days.

(21) Appl. No.: 16/733,840

(22) Filed: Jan. 3, 2020

(65) Prior Publication Data
US 2020/0138965 A1    May 7, 2020

Related U.S. Application Data (62) Division of application No. 15/072,871, filed on Mar. 17, 2016, now abandoned.

(30) Foreign Application Priority Data

Mar. 17, 2015    (KR) .................. 10-2015-0036992

(51) Int. Cl.
| A61K 47/61 | (2017.01) |
| A61K 9/51 | (2006.01) |
| A61K 9/00 | (2006.01) |

(52) U.S. Cl.
CPC ............ *A61K 47/61* (2017.08); *A61K 9/0019* (2013.01); *A61K 9/51* (2013.01)

(58) Field of Classification Search
CPC ......... A61K 9/51; A61K 46/61; A61K 9/0019
USPC ......................................................... 514/26
See application file for complete search history.

(56) References Cited

U.S. PATENT DOCUMENTS

| 7,511,023 B2 * | 3/2009 | Kwon .................. A61K 31/704 514/34 |
| 8,604,023 B2 | 12/2013 | Glick | |

FOREIGN PATENT DOCUMENTS

| KR | 10-2003-0015926 | 2/2003 | |
| KR | 10-2015-0036992 | 5/2017 | |
| WO | WO 2006/113495 | 10/2006 | |
| WO | WO 2006/113495 A | * 10/2006 | ........... A61K 31/575 |

OTHER PUBLICATIONS

Sparer et al, Controlled Release from Glycosaminoglycan Drug Complexes, chapter 6, in Controlled Release Delivery lSystems, New York, 1983, pp. 107-119.*
Felt et al., "Chitosan: a unique polysaccharide for drug delivery", Drug Development and Industrial Pharmacy, 24(11): 979-993, 1998.
Goodarzi et al., "A review of polysaccharide cytotoxic drug conjugates for cancer therapy", Carbohydrate Polymers, 92: 1280-1293, 2013.
Mathiyalagan et al., "Ginsenoside compound K-bearing glycol chitosan conjugates: synthesis, physicochemical characterization, and in vitro biological studies", Carbohydrate Polymers, 112: 359-366, 2014.
Mathiyalagan et al.,"Insilico profiling of microRNAs in Korean ginseng (Panax ginseng Meyer)", Journal of Ginseng Research, 37(2): 227-247, 2013.
Mathiyalagan et al., "Synthesis and pharmacokinetic characterization of a pH-sensitive polyethylene glycol ginsenoside CK (PEG-CK) conjugate", Bioscience, Biotechnology, and Biochemistry, 78(3): 466-468, 2014.
Mathiyalagan et al., "Synthesis of ginsenoside compound K with glycol chitosan and polyethylene glycol conjugates—in vitro biological studies", 2014 Spring Ginseng Conference of the Korean Society of Ginseng, Oral presentation, Apr. 29, 2014.
Chen et al., "Anti-cancer effects of ginsenoside compound k on pediatric acute myeloid leukemia cells", Cancer Cell International, 13:24, 2013.
Sparer, R. V., N. Ekwuribe, and A. G. Walton. "Controlled release from glycosaminoglycan drug complexes." Controlled Release Delivery Systems. Dekker New York, 1983. 107-119.
Official Action received in U.S. Appl. No. 15/072,871 dated Aug. 11, 2017.
Official Action received in U.S. Appl. No. 15/072,871 dated Mar. 1, 2018.
Official Action received in U.S. Appl. No. 15/072,871 dated Dec. 27, 2018.
Official Action received in U.S. Appl. No. 15/072,871 dated Sep. 3, 2019.

* cited by examiner

*Primary Examiner* — Ganapathy Krishnan
(74) *Attorney, Agent, or Firm* — Parker Highlander PLLC (57) ABSTRACT

The present invention relates to a conjugate of ginsenoside compound K and glycol chitosan, a method for preparing the conjugate, and a pharmaceutical composition for treating cancer including the conjugate in a pharmaceutically acceptable carrier. The conjugate of ginsenoside compound K and glycol chitosan of the present invention has cancer cell-specific anticancer activity because of increased water solubility relative to ginsenoside compound K, formation of nanosized self-aggregates in an aqueous solution, stability at neutral pH and release of the ginsenoside compound K at acidic pH due to pH sensitivity, thus having excellent effects as a composition for treating cancer.

5 Claims, 8 Drawing Sheets

CONJUGATE OF GINSENOSIDE COMPOUND K AND GLYCOL CHITOSAN AND AN ANTI-TUMOR USE THEREOF

This application is a divisional of U.S. Ser. No. 15/072,871, filed Mar. 17, 2016, which claims benefit of priority to Korean Application No. 10-2015-0036992 filed Mar. 17, 2015, the entire contents of each of which are hereby incorporated by reference.

TECHNICAL FIELD

The present invention relates to a conjugate of ginsenoside compound K and glycol chitosan, a method for preparing the conjugate, and a pharmaceutical composition for treating cancer including the conjugate in a pharmaceutically acceptable carrier.

BACKGROUND ART

Cancer is a leading cause of death worldwide. Although anticancer drugs having high activities for cancer treatment are available, the use in cancer chemotherapy is limited due to the problems such as low specificity to cancer cells, low water-solubility, cytotoxicity, a short half-life in the bloodstream, etc.

Numerous drug delivery carriers such as conjugates of polymers and drugs, micelles, nanoparticles, and stealth liposomes have been reported for efficient drug delivery. For example, cancer drugs encapsulated with nanosized drug carrier exhibit improved efficacy compared to non-treated anticancer drugs. Further, squalenoyl-based natural triterpene drug conjugates formed self-assembled nanoparticles, thus anticancer activity has been improved.

Among these, a method for conjugating water-soluble polymers with anticancer drugs has been specifically proposed as a way of solving the problems of the cancer chemotherapy (Carbohydrate Polymers, 2013, 92(2), 1280-1293). When the water-soluble polymer is conjugated with anticancer drugs, effects such as enhanced water-solubility of hydrophobic drugs and prolonged circulation time of drugs in the bloodstream, as well as reduced cytotoxicity for normal cells, prevention of deactivation of drugs, increased accumulation in tumor tissues as a result of enhanced permeation and retention (EPR), etc., may be expected.

On the other hand, polysaccharides have gained attention as a potent drug delivery vehicle due to their ideal physiochemical and biological properties (Drug Development and Industrial Pharmacy, 1998, 24(11), 979-993). Specifically, among the above polysaccharides, chitosan is known to have excellent biodegradability, biocompatibility, mucoadhesive interaction with the intestinal track, antibacterical activity, antifungal activity, and antioxidant activity. Chitosan is a natural biopolymer composed of β-1, 4 linked N-acetyl-D-glucosamine and D-glucosamine and is prepared by deacetylation of chitin. Chitin, which is one of the most abundant natural polysaccharides, forms crustaceans, shells of molluscs, cuticles of insects, cell walls of fungi, etc. The use of organic acids to dissolve chitosan for drug delivery application causes side effects, and therefore, $CO_2$ and alkaline $NH_4HCO_3$ were used to dissolve chitosan while yielding thin films or gels.

With respect to the chitosan, hydrophilic chitosan derivatives, such as glycol chitosan (GC) and carboxymethyl chitosan, have been developed. In particular, due to the biocompatibility and good water-solubility over a wide range of pH levels, GC has been extensively studied as a hydrophilic carrier for a variety of drugs and proteins.

*Panax ginseng* has been traditionally used as a medicinal herb in oriental medicine in Korea, China, and Japan. The main active component of *Panax ginseng* is ginsenoside, which is triterpene saponin (Journal of Ginseng Research, 2013, 37(2), 227-247). Ginsenosides are broadly classified as protopanaxadiols (PPD) and protopanaxatriols (PPT), and more specifically, into major and minor ginsenosides based on the steroidal sapogenin and number of sugar chains and linkages, all of which account for the diverse bioactivities of the compounds. Ginsenosides are reported to exhibit efficacies such as anticancer and antiinflammatory effects, as well as effects against Alzheimer's disease and diabetes.

Specifically, ginsenoside compound K (20-O-β-(D-glucopyranosyl)-20(S)-protopanaxadiol) even among the geinsenoside, has gained a special attention because of unique biological properties. The ginsenoside compound K is one of the primary metabolites obtained after oral administration of PPD-type ginsenosides by intestinal enzymes and has various pharmacological properties including induction of apoptosis and inhibition of proliferation in human colorectal cancer cells and hepatoblastoma HepG2 cells. Further, the ginsenoside compound K inhibits proinflammatory cytokines in lipopolysaccharide (LPS)-stimulated macrophages.

Despite the above useful properties reported, ginsenoside compound K has problems in that it has low water solubility and a difficulty in target-specific delivery to tumor sites, thereby causing side effects by exhibiting toxicities in normal cells. The present inventors have made extensive efforts to solve the problems, and as a result, they have prepared a conjugate of ginsenoside compound K and glycol chitosan and confirmed that the conjugate has increased water solubility and cancer cell-specific activity compared to the ginsenoside compound K, thus completing the present invention.

SUMMARY OF THE INVENTION

The present invention relates to a conjugate of ginsenoside compound K and glycol chitosan, a method for preparing the conjugate, and a pharmaceutical composition for treating cancer including the conjugate in a pharmaceutically acceptable carrier.

The conjugate of ginsenoside compound K and glycol chitosan of the present invention has cancer cell-specific anticancer activity because of increased water solubility relative to ginsenoside compound K, formation of nanosized self-aggregates in an aqueous solution, stability at neutral pH and release of the ginsenoside compound K at acidic pH due to pH sensitivity, thus having excellent effects as a composition for treating cancer.

BEST MODE FOR CARRYING OUT THE INVENTION

The present invention relates to a conjugate of ginsenoside compound K and glycol chitosan, a method for preparing the conjugate, and a pharmaceutical composition for treating cancer including the conjugate in a pharmaceutically acceptable carrier.

In an aspect to achieve the above objects, the present invention provides a conjugate of the ginsenoside Compound K and glycol chitosan.

As used herein, the term "ginsenoside compound K", which is absent in *Panax ginseng* itself, refers to saponin in which saponins such as ginsenoside Rb1, Rb2, Rc, Rd, etc., in *Panax ginseng* or *Ginseng Radix Rubra* are transformed into the form that can be absorbed into the body by intestinal microorganisms including bifidobacteria or soil microorganismal actions, and is represented by the following Formula 1.

Formula 1

In the present invention, commercially available ginsenoside compound K may be purchased or the one transformed from ginsenoside isolated from *Panax ginseng* grown or obtained from the nature may be used, or the ginsenoside compound K synthesized by a synthetic method may be used, but is not limited as long as the ginsenoside compound K showing the effects for treating cancer of the present invention is used.

According to what has been studied so far, the ginsenoside compound K is reported to show antiinflammatory effects (Park E K, et al., Biol. Pharm. Bull., 28:652-656, 2005), hepatoprotective effects (Lee H U, et al., Liver Int., 25:1069-1073, 2005), effects for treating liver fibrosis (Park E J, et al., Planta Med., 72:1250-1253, 2006), effects for inhibiting tumor proliferation (Jung S H, et al., Int. J. Cancer, 118-490-497, 2006), antioxidative effects (Bae E A, et al., Arch. Pharm. Res., 27:1136-1140, 2004), antiallergic effects (Choo M K, et al., Planta Med., 69:518-522, 2003), effects for preventing neurodegenerative diseases (Tohda C., et al., Neuropsychopharmacology, 29:860-868, 2004), effects for protecting the skin (Shin Y W, et al., J. Pharmacol. Sci., 99:83-88, 2005), etc. However, the ginsenoside compound K had low water solubility and toxicity towards cancer cells as well as normal cells, which limited its use for anticancer drugs. Therefore, in the present invention, a conjugate with glycol chitosan was prepared to increase the water solubility and induce cancer cell-specific activity of the ginsenoside compound K, thus completing the present invention. Although the ginsenoside compound K has low water solubility, has no specificity to cancer cells, and glycol chitosan has no anticancer activities, the above disadvantages have been overcome by the conjugation of the two compounds.

As used herein, the term "glycol chitosan", which is one of the water-soluble chitosan derivatives, shows water-solubility at neutral pH by the introduction of hydrophilic ethylene glycol group. Chitosan, which is a basic polysaccharide prepared by treating chitin with a high concentration of alkali followed by N-deacetylation, is known to have excellent cell adsorptivity, biocompatibility, biodegradability, moldability, etc., compared to other synthetic polymers. In addition, glycol chitosan shows non-cytotoxicitiy, biocompatibility, and can stimulate the growth of chondrocytes at a low concentration. Glycol chitosan used in the present invention may have a molecular weight ranging from 200,000 to 600,000 and the degree of deacetylation may range from 60% to 90%, but is not limited thereto.

As used herein, the term "conjugate" refers to the form chemically conjugated by the ginsenoside compound K and glycol chitosan.

To prepare the conjugates of the ginsenoside compound K and glycol chitosan, the ginsenoside compound K of the present invention may be carboxylated and the conjugates may have been prepared after the carboxylated ginsenoside compound K forms an amide bond with glycol chitosan.

In another aspect, the present invention provides a method for preparing a conjugate of ginsenoside compound K and glycol chitosan, including:

(a) carboxylating the ginsenoside compound K; and (b) conjugating the carboxylated ginsenoside compound K and glycol chitosan.

The ginsenoside compound K, glycol chitosan, and the conjugate thereof are the same as described above.

The step (a), which involves transforming ginsenoside for the ginsenoside compound K to covalently bond with glycol chitosan, may be a step for substituting an alcohol group that is present in cyclohexane ring of the ginsenoside compound K with hydrocarbon having a carboxyl group at terminus. Specifically, the carboxylation may be induced by succinic anhydride, but is not limited thereto.

The step (b), which involves binding the carboxylated ginsenoside compound K with glycol chitosan, is a step for forming an amide bond after the amine group of glycol chitosan reacts with the carboxyl group of the carboxylated ginsenoside compound K.

Figure 1A:
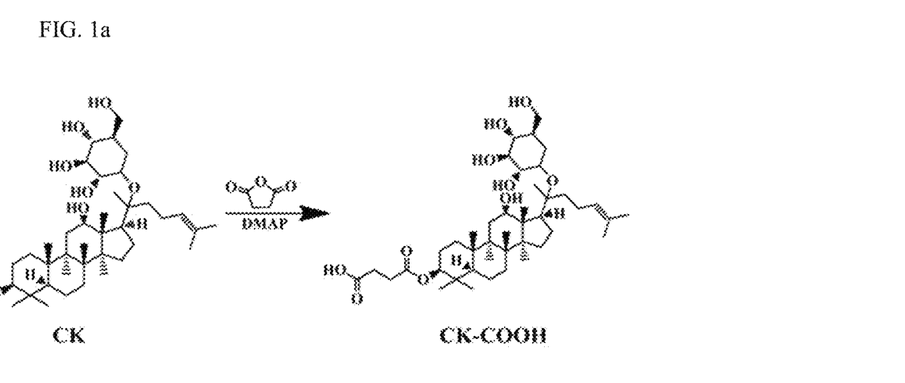
FIGS. 1a and 1b show a synthetic route for the preparation of GC-CK conjugates. (a) is a procedure for preparing CK into CK-COOH and (b) is a procedure for preparing GC-CK using CK-COOH.
Figure 1B:
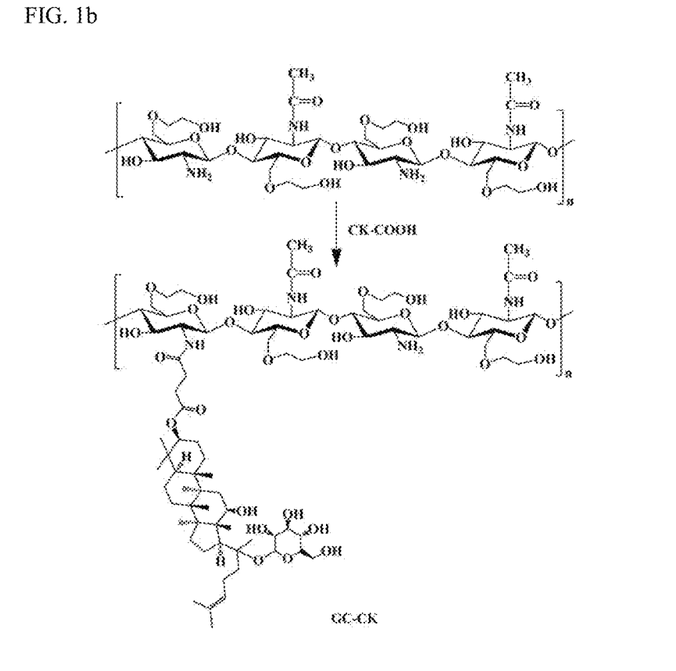

In an exemplary embodiment of the present invention, the ginsenoside compound K was treated with succinic anhydride to prepare the carboxylated ginsenoside compound K, which could form an amide bond through the reaction with glycol chitosan, thus preparing the conjugates of the ginsenoside compound K and glycol chitosan (FIGS. 1a and 1b).

Figure 3:
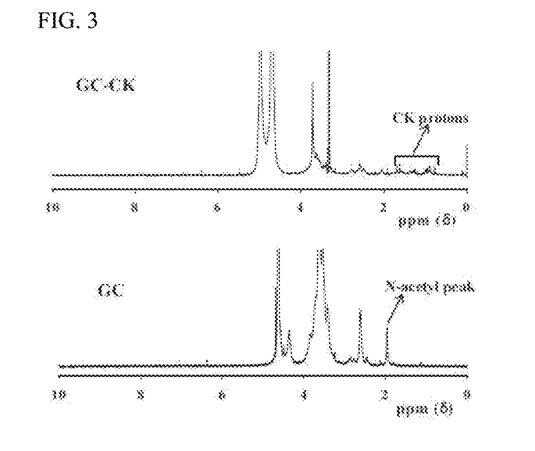
FIG. 3 shows $^1$H NMR spectra of the GC-CK conjugate and GC.
Figure 4:
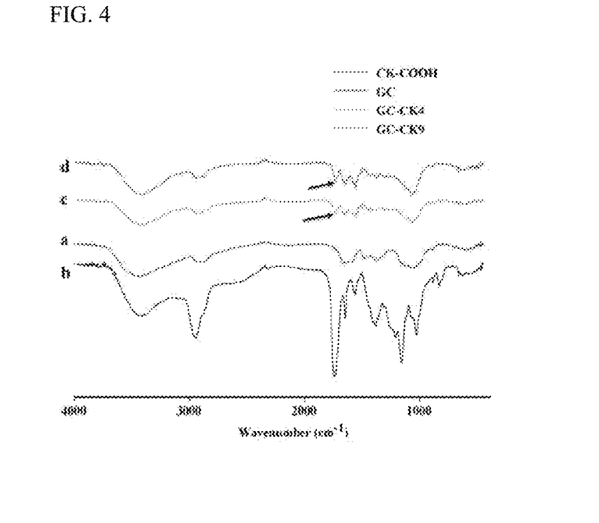
FIG. 4 shows FT-IR spectra of (a) GC, (b) CK-COOH, (c) GC-CK4, and (d) GC-CK9.

In an exemplary embodiment of the present invention, it was confirmed that the conjugates of the ginsenoside compound K and glycol chitosan generated by the preparation method was successfully prepared through $^1$H NMR (FIG. 3) and FT-IR (FIG. 4).

As used herein, the term "self-aggregate" indicates that molecules voluntarily form an organized structure, respectively, and generally have a specific form. In general, in order for molecules to form self-aggregates, each molecule should have a structural feature and a noncovalent binding force between the molecules should be present. The conjugates may form self-aggregate in an aqueous solution, which may be formed due to the fact that the ginsenoside compound K has hydrophobicity while glycol chitosan has hydrophilicity. As such, the sites having hydrophobicity in the molecules aggregate towards the inside in an aqueous solution and the sites having hydrophillicity line up on the outside, which faces the aqueous solution, and therefore, spherical self-aggregates may be formed.

The self-aggregate is not limited thereto, but may specifically have a diameter ranging from 100 nm to 700 nm.

Figure 5A:
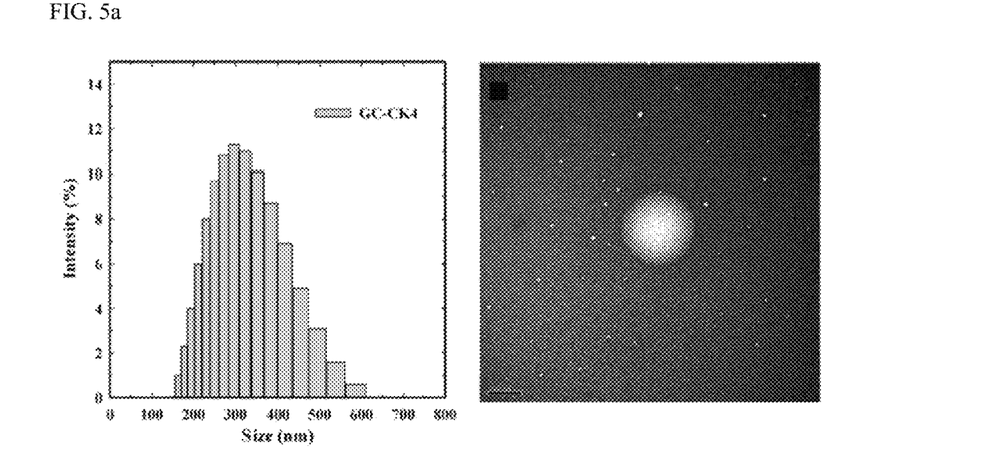
FIGS. 5a and 5b show the particle sizes of GC-CK conjugates: (a) GC-CK4 and (b) GC-CK9. The spherical-shaped GC-CK conjugates were observed in TEM images. The scale bar represents 200 nm.
Figure 5B:
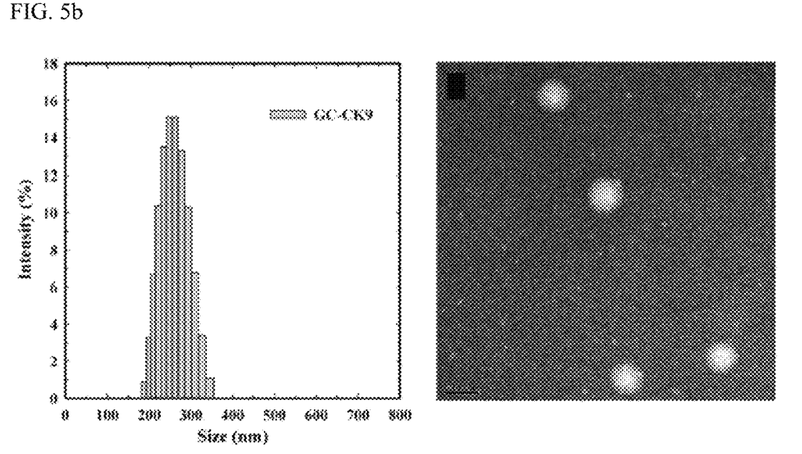

In an exemplary embodiment of the present invention, it was confirmed that a conjugate of the ginsenoside compound K and glycol chitosan formed spherical self-aggregates in TEM photograph and the size of self-aggregates based on the molar ratio of the ginsenoside compound K was confirmed by a particle analyzer (FIGS. 5a and 5b).

The conjugate may include an ester linkage in binding sites. Because an ester (—COO—) can be decomposed in an acidic condition, the conjugates can have properties capable of releasing the ginsenoside compound K at a pH between 4.0 and 6.0 and maintaining stability at least for 8 days at a pH between 7.0 and 8.0.

Figure 6:
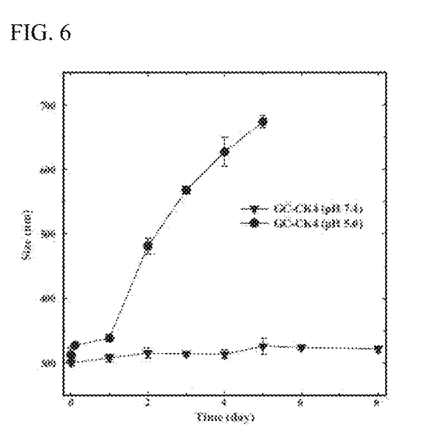
FIG. 6 shows stability of GC-CK conjugates based on pH of buffer solutions. The error bar represents standard deviation (n=3).

In an exemplary embodiment of the present invention, as the result of confirming the stability of the conjugates based on pH, the size of the conjugate became gradually increased at pH 5.0, but the conjugate remained in an stable form for 8 days at pH 7.4 (FIG. 6).

Figure 7:
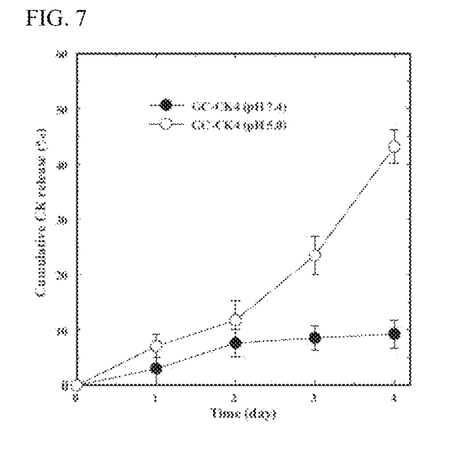
FIG. 7 shows CK release from GC-CK conjugates based on pH of buffer solutions. The error bar represents standard deviation (n=3).

In another exemplary embodiment of the present invention, as the result of confirming the release behavior of the ginsenoside compound K in the conjugate based on pH, there was almost no release at pH 7.4 even after 4 days have passed, but the release amount considerably increased at pH 5.0 as a function of time (FIG. 7).

Therefore, because the conjugate of the ginsenoside compound K and glycol chitosan has pH sensitivity by including an ester linkage, it has properties of releasing the ginsenoside compound K due to stability at neutral pH and the decomposition of the ester linkage at acidic pH. As a result, the conjugate having stability can circulate for a prolonged time in the bloodstream that is neutral. In addition, cancer cells have specifity to release the ginsenoside compound K because pH in cancer cells are more acidic than that in normal cells. Therefore, the conjugate of the ginsenoside compound K and glycol chitosan of the present invention has excellent effects as a composition for target-specific cancer therapy.

In another aspect, the present invention provides a pharmaceutical composition for treating cancer including the conjugate of the ginsenoside compound K and glychol chitosan in a pharmaceutically acceptable carrier.

The ginsenoside compound K, glycol chitosan, and the conjugates thereof are the same as described above.

As used herein, the term "cancer" is included without any limitations regardless of types of cancers, but the examples may include esophageal cancer, stomach cancer, colorectal cancer, rectal cancer, oral cavity cancer, pharynx cancer, larynx cancer, lung cancer, colon cancer, breast cancer, uterine cervical cancer, endometrial cancer, ovarian cancer, prostate cancer, testis cancer, bladder cancer, kidney cancer, liver cancer, pancreatic cancer, bone cancer, connective tissue cancer, skin cancer, brain cancer, thyroid cancer, leukemia, Hodgkin's disease, lymphoma, multiple myeloma blood cancer, and more preferably the cancer may be colorectal cancer, liver cancer, and brain cancer.

In an exemplary embodiment of the present invention, the cytotoxicity of the conjugates of the ginsenoside compound K and glychol chitosan was confirmed by HT-29, which is a colorectal cancer cell line, HepG2, which is a liver cancer cell line, and HT22, which is a brain cancer cell line, (FIGS. 8b to 8d), thereby confirming that the conjugates have anticancer activities.

As used herein, the term "treatment" refers to all the activities by which the symptoms caused by cancer become improved or beneficially changed by administering the composition to a subject suspected of having cancer.

The pharmaceutical composition of the present invention may be used as a single formulation or a combination formulation by further including other therapeutic methods or drugs known to have authorized effects for treating cancer, and may be prepared in a unit dosage formed by the formulation with a pharmaceutically acceptable carrier or excipient, or prepared by the introduction into a heterogeneous container. Further, in terms of the therapeutic methods, the pharmaceutical composition of the present invention may be administered simultaneously or sequentially with other therapeutic method(s) or formulation(s).

As used herein, the term "pharmaceutically acceptable carrier" may refer to a carrier or diluent, which does not irritate organisms and interrupt biological activities and properties of the injected compounds. The types of the carriers to be used in the present invention are not specifically limited and any carrier that is conventionally used and pharmaceutically acceptable in the technical field may be used. Non-limiting examples of the carriers may include saline solution, sterilized water, Ringer's solution, buffered saline solution, albumin injection solution, dextrose solution, maltodextrine solution, glycerol, ethanol, etc. They may be used alone or in combination of at least 2 types. The carriers may include non-naturally occurring carriers. Further, if required, other conventional additives such as antioxidants, buffered solution and/or bacteristats, etc., may be added for use, and diluents, dispersants, surfactants, binders, lubricants, etc., may further be added and formulated into injection formulations such as an aqueous solution, a suspension, an emulsion, etc., pills, capsules, granules, tablets, etc., for use.

In addition, the pharmaceutical composition of the present invention may include a pharmaceutically effective amount of the conjugate of the ginsenoside compound K and glycol chitosan. As used herein, the term "pharmaceutically effective amount" refers to a sufficient amount for treating diseases at a reasonable benefit/risk ratio applicable for medical treatment and may be administered once or several times per day generally in an amount ranging from 0.001 mg/kg to 1000 mg/kg, preferably 0.05 mg/kg to 200 mg/kg, and more preferably 0.1 mg/kg to 100 mg/kg. However, with respect to the purpose of the present invention, it is preferable to differently apply a specific and medically effective amount for specific patients depending on the types and degrees of desired reactions, the fact determining whether different formulations such as specific composition are used for different situations, age, weight, general health condition, gender, diet of the patient, administration time, administration route, secretion rate of the composition, drugs used together or simultaneously with the specific composition, various factors, and similar factors well-known in the medical field.

The pharmaceutical composition of the present invention may be administered as an individual medicine or in combination with other medicine, and administered sequentially or simultaneously with the existing medicine. Then, the pharmaceutical composition may be administered in single or multiple doses. Considering all the elements above, it is important to administer the minimum amount, which can obtain the maximum effects without causing side effects, and this may be readily determined by one of ordinary skill in the art.

As used herein, the term "administration" refers to introducing the pharmaceutical composition of the present invention to a patient by proper methods. The administration route of the composition of the present invention may include administering through various routes including oral or parenteral routes as long as it can reach the desired tissues.

The administration method of the pharmaceutical composition of the present invention is not particularly limited and may follow the methods conventionally used in the technical field. Non-limiting examples of the administration methods may include administering the composition in an oral administration or a parenteral administration, and specifically have the purpose in oral, intracranial, intraspinal, digestive tract, or parenteral administrations. The pharmaceutical composition according to the present invention may be prepared in various forms based on desired administration methods.

The administration frequency of the composition of the present invention is not specifically limited thereto, but may be administered once or in a few divided doses daily.

In an exemplary embodiment of the present invention, to determine the specific effects of the conjugates on cancer treatment, cell viability was confirmed when various types of cell lines were treated with glycol chitosan, ginsenoside compound K or the conjugates thereof. As a result, it was confirmed that cell viability was not affected when treated with glycol chitosan (FIG. 8a), and although the conjugates exhibited the effect of considerably reducing viability due to their cytotoxicity against cancer cell lines (FIGS. 8b to 8d), they did not affect viability in normal cell lines (FIG. 9a), and reduced NO caused by lipopolysaccharide (LPS) treatment (FIG. 9b). Therefore, the conjugates of ginsenoside compound K and glycol chitosan of the present invention shows activities that are specific to cancer cells, thus having excellent effects as a composition for target-specific cancer therapy.

In another aspect, the present invention provides a method for preventing or treating cancer including administering the pharmaceutical composition to a subject.

The pharmaceutical composition, administration, and cancer treatment are the same as described above.

As used herein, the term "subject" refers to all the animals including humans having cancer or having the risk of cancer development. The animals may include humans, as well as mammals, such as cows, horses, sheep, pigs, goats, camels, antelopes, dogs, cats, etc., in need of treatment for similar symptoms, but are not limited thereto.

The method for treatment of the present invention may specifically include administering the composition to a subject having cancer or having the risk of cancer development in a pharmaceutically effective amount.

Hereinafter, the present invention will be described in details with reference to the following Examples. However, the Examples of the present invention may be embodied in many different forms and the scope of the present invention is not limited to these Examples. The Examples of the present invention are provided for one of ordinary skill in the art to better understand the present invention.

Example 1: Materials

Glycol chitosan (GC, Mw=4.3×10$^5$, degree of deacetylation=75.2%), N-hydroxyl succinimide, (NHS), succinic anhydride, 1-ethyl-3-(3-dimethylaminopropyl)-carbodiimide.hydrochloride (EDC·HCl) were purchased from Sigma-Aldrich (St. Louis, Mo., USA). Compound K (CK) was purchased from Ginseng Genetic Resource Bank (Kyung Hee University, Yongin, Korea).

Example 2: Synthesis of GC-CK Conjugates

Figure 2:
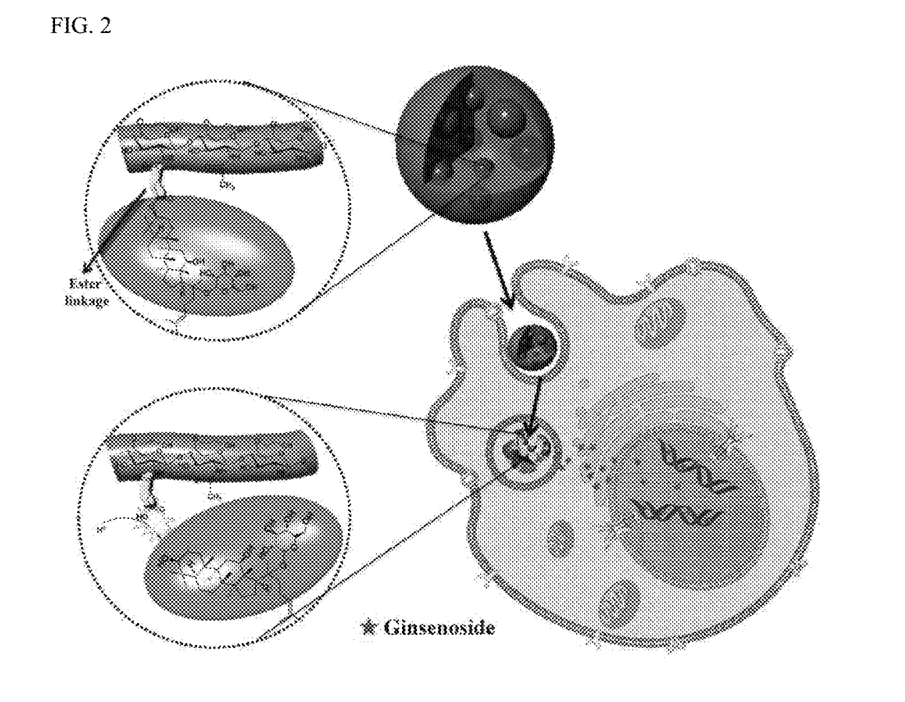
FIG. 2 shows a schematic diagram of CK release from GC-CK conjugate at the intracellular environment.

A conjugate of ginsenoside CK and glycol chitosan (GC) was prepared by an ester linkage, which was hydrolyzed under acidic conditions to increase solubility and cancer cell specificity of hydrophobic ginsenoside CK and release CK for the purpose of treatment. The synthetic procedure used for this purpose are shown in FIGS. 1a and 1b. Further, the operating principle of GC-CK conjugate is shown in FIG. 2.

Specifically, the synthesis of GC-CK was achieved via a two-step process in which the carboxylated CK (CK-COOH) was prepared and conjugated to the GC through an amide bond (FIGS. 1a and 1b). CK (0.01 g, 0.016 mmol) was dissolved in 2 mL of pyridine/dichloromethane (1:1), to which succininc anhydride was added and reacted for 24 hours at room temperature. Then, the solvent was evaporated, precipitated, filtered, washed, and dried under vacuum to obtain CK-COOH powder. Next, GC (0.1 g, 0.53 mmol) was dissolved in 8 mL of distilled water and diluted with 24 mL of methanol, after which CK-COOH (0.038 g, 0.053 mmol), EDC (0.04 g, 0.21 mmol), and NHS (0.024 g, 0.21 mmol) were added and stirred for 24 hours at room temperature. The mixture was transferred to a dialysis membrane (MWCO: 14,000) and dialyzed against an excess amount of methanol/distilled water (75:25, v/v) for 1 day and distilled water for 2 days. Thereafter, the dialyzed solution was lyophilized to obtain the GC-CK conjugates.

Example 3: Structural Analysis of GC-CK Conjugates

The structures of the GC-CK conjugates were confirmed by $^1$H NMR and FT-IR to confirm whether the GC-CK conjugates were successfully prepared. NMR spectra were recorded at 300 MHz (JEOL, Tokyo, Japan). Each sample was dissolved in D$_2$O or CD$_3$OD. FT-IR spectra of the conjugates were recorded by a Perkin-Elmer FT-IR spectrophotometer using KBr pellets.

FIG. 3 shows $^1$H NMR data of GC-CK conjugates, which exhibits the characteristic peaks of GC and CK. The degree of substitution (DS), defined as the number of CK's in 100 repeating sugar units, was calculated based on the integration ratios of the proton peak appearing from the methyl group of CK at 0.68 ppm to that of the N-acetyl peak of GC at 2 ppm. Two types of GC-CK conjugates were prepared by varying the feed molar ratio of CK to GC. As expected, the DS increased as the feed ratio increased (i.e., for 0.1 and 0.2 molar ratio of CK, the conjugates with a DS of 4 and 9 were obtained, respectively). The synthesized GC-CK conjugates were coded dependent on the DS value. For example, GC-CK4 indicates a conjugate in which the DS of the CK is 4.

FIG. 4a shows the FT-IR spectrum of GC and includes characteristic peaks of 3441 cm$^{-1}$ (O—H stretch overlapped with N—H stretch), 2880 cm$^{-1}$ (aliphatic C—H stretch), 1659 cm$^{-1}$ (amide 1 band, C=O stretch of acetyl group), 1470-1382 cm$^{-1}$ (C—H bend), and 1066 cm$^{-1}$ (skeletal vibrations involving the C—O stretch). The FT-IR spectra of CK-COOH confirmed the presence of a very intense carboxylic C=O bond at 1740 cm$^{-1}$, which showed esterification of CK (FIG. 4b). Compared with GC, the increased peak at 1733 cm$^{-1}$ in GC-CK conjugates (FIGS. 4c and 4d) indicated the presence of carbonyl bond. In addition, the increase in peak at 1558 cm$^{-1}$ (amide II band, N—H bending) and 1653 cm$^{-1}$ (amide I band) showed the formation of amide bonds between CK-COOH and GC.

In conclusion, it was confirmed that GC-CK conjugates were successfully prepared by the amide bonds between CK-COOH and GC.

Example 4: Analysis on Size, Morphology, and Stability of GC-CK Conjugates

Due to the amphiphilic nature, GC-CK drug conjugates could form self-assembled nanoparticles in an aqueous solution environment. Thus, a GC hydrophilic shell could cover a hydrophobic CK core and protect it from proteolytic digestion to allow for prolonged circulation in the bloodstream. To confirm the properties of the GC-CK conjugates, analyses on size, morphology, and stability of the conjugates were conducted.

The morphology of conjugates was observed using FE-TEM operated at an acceleration voltage of 200 kV. To prepare TEM samples, one drop of the sample solution was placed onto a 200-mesh copper grid coated with carbon and allowed to air dry. A drop of phosphotunstic acid solution was dropped to be used as a negative control. The size distribution and stability of conjugates were determined by a particle analyzer, for which each sample was dispersed in either phosphate-buffered saline (PBS, pH 7.4) or acetate buffer (pH 5.0).

Initially, as the result of confirming the size of the conjugates, the average diameters of the conjugates of GC-CK4 and GC-CK in aqueous media were 296 nm and 255 nm, respectively (FIGS. 5a and 5b). The size of the nanoparticles decreased as the amount of hydrophobic CK increased, which was attributed to stronger hydrophobic interactions.

Next, as the result of confirming the morphology of the conjugates using FE-TEM, it was confirmed that the conjugates formed spherical-shaped particles in aqueous media due to the outer hydrophilic GC and inner hydrophobic CK (FIGS. 5a and 5b).

On the other hand, various features such as molecular weight, particles size, blood circulation time, and stability are all important factors that contribute to the delivery of nanoparticles to tumor tissues. Thus, the stabilities of the GC-CK conjugates were confirmed by measuring the particle size at 37° C. in PBS (pH 7.4) as function of time. The stability of GC-CK4 conjugates was maintained for 8 days, indicating their thermodynamic stability in aqueous media. In addition, nanoparticle size was increased in acidic conditions (pH 5.0), primarily due to the hydrolysis of CK from conjugates, resulting in the formation of large aggregates by the hydrolyzed CK through hydrophobic interaction (FIG. 6).

From the experiment above, it was observed that the GC-CK conjugates of the present invention formed spherical-shaped nanoparticles and had high stability in physiological buffer solution, indicating that the conjugates can circulate for a prolonged time in the body.

Example 5: Confirmation of pH-Dependent CK Release from GC-CK Conjugates

Polymer conjugated macromolecular prodrugs have the ability to reach cancer tissues due to their leaky vasculature. Further, target drugs may be released at cancer tissues following their exposure to intracellular stimuli. In particular, pH-responsive drug conjugates have gained increased attention due to the difference in pH between normal tissues and cancer tissues. Specifically, the intracellular pH of cancer cells (pH 5.0 to 6.5) is usually much lower than physiological pH conditions (pH 7.4). CK release behavior from the GC-CK conjugates was monitored by incubating samples at pH 7.4 (physiological conditions) and pH 5.0 (pathophysiological conditions) as a function of time. The specific details of the experimental methods are as follows.

GC-CK conjugates (3 mg/mL) were mixed in 1 mL of distilled water and transferred to cellulose membrane tubes (MWCO: 14,000). The dialysis membrane was then placed in either 30 mL of PBS (pH 7.4) or acetate buffer (pH 5.0) and the samples were gently shaken at 37° C. at 120 rpm. At pre-determined time intervals, samples were removed by 5 mL and replaced with a fresh medium. To observe the amount of hydrolyzed CK, the solution was extracted three times with water-saturated n-BuOH and evaporated. Then, the amount of CK present in the samples were monitored by HPLC [Agilent, C18 column (3.0×50 mm, particle size 2.7 µm)] with acetonitrile (solvent A) and distilled water (solvent B) as mobile phases, at 81% B and 19% A for 0 minutes, 81% B and 19% A for 7 minutes, 71% B and 29% A for 11 minutes, 71% B and 29% A for 14 minutes, 60% B and 40% A for 25 minutes, 44% B and 56% A for 28 minutes, 30% B and 70% A for 30 minutes, 10% B and 90% A for 31.5 minutes, 10% B and 90% A for 34 minutes, 81% B and 19% A for 34.5 minutes, and 81% B and 19% A for 40 minutes, all at a flow rate of 1.0 mL/min. The injection volume of each sample was 5 µL. UV detection was performed at 203 nm.

As the result of HPLC, it was confirmed the percentage of CK release was enhanced at pH 5.0 compared with at pH 7.4 (FIG. 7). Because the GC-CK conjugate was synthesized via an acid-labile ester linkage, it indicated that the hydrolysis would occur in solid cancer tissues, endosomes, and lysosomes through the hydrolysis that occurs in a slightly acidic buffer solution. Therefore, selective pH release by ester linkages present in the GC-CK conjugates may be effective for targeted delivery of CK to pathophysiological sites such as cancers.

Example 6: Confirmation of Cytotoxicity for Normal Cells and Cancer Cells

To observe the anticancer activity of the GC-CK conjugates, the cytotoxicity of pure GC, CK, and GC-CK conjugates were confirmed in anticancer cells by MTT assay.

Specifically, the HT-29 (human colon cancer) cell line was purchased from the Korean Cell Line Bank (Seoul, Korea) and cultured in RPMI 1640 medium (Welgene, Inc.) containing 1% (w/v) penicillin-streptomycin (Welgene, Inc.) and 10% (v/v) FBS (Welgene, Inc.) in 5% $CO_2$ and 95% humidity at 37° C. The cells were inoculated at a density of $2 \times 10^4$ cells/well in 96-well plates (SPL Life Sciences, Korea). After growing for 24 h, the culture medium was replaced with the culture medium containing 100 µL, of various concentrations of GC, standard GC, and GC-CK and cultured for 24 h at 37° C. Next, 10 µL of 3-(4, 5-dimethylthiazol-2-yl)-2, 5-diphenyl-tertazolium bromide) (MTT) was added and the plates were cultured for 3 hours at 37° C. The culture medium was then removed and blue formazan crystals were dissolved with 100 µL of DMSO. The optical density was measured at 570 nm using a Synergy HT multidetection microplate reader (Molecular Devices, BioTek Instruments, Winooski, Vt., USA). Similarly, the MTT assay was performed in HepG2 and HT22 cell lines as described above. Cytotoxicity lipopolysaccharide (LPS)-induced NO analysis was conducted in RAW264.7 (murine macrophage) cells.

Figure 8A:
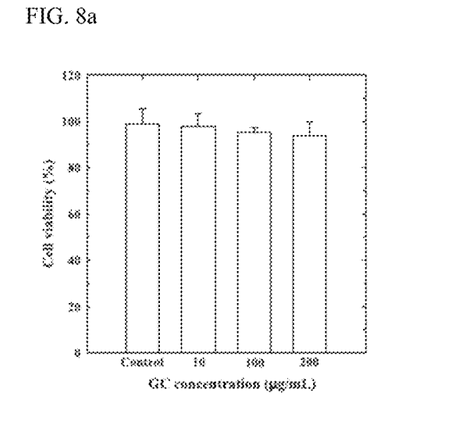
FIGS. 8a to 8d show cytotoxicity of GC and GC-CK conjugates. The cytotoxicity of GC and GC-CK conjugates for (a) HT29 cell line, (b) HT29 cell line, (c) HepG2 cell line, and (d) HT22 cell line was confirmed. The error bar represents standard deviation (n=3) (**P<0.0001, *P<0.001, and **P<0.01). Curcumin (20 μM) and Trolox were used as positive controls and t-BHP and GA were used as negative controls.
Figure 8B:
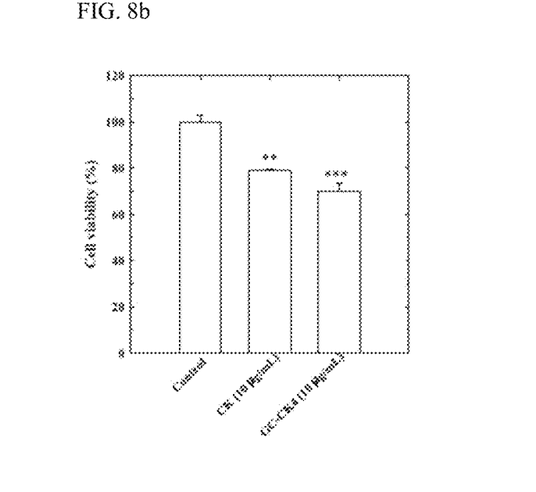
Figure 8C:
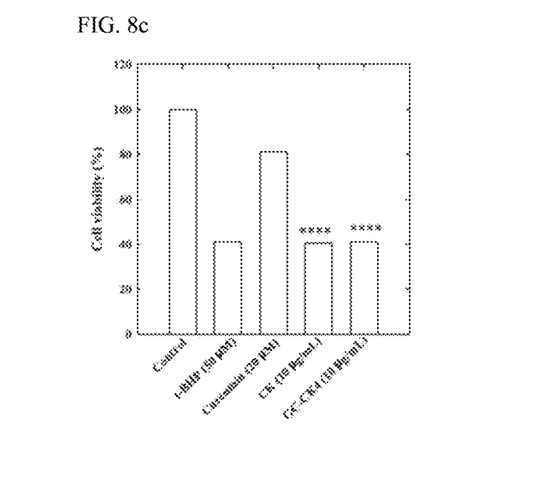
Figure 8D:
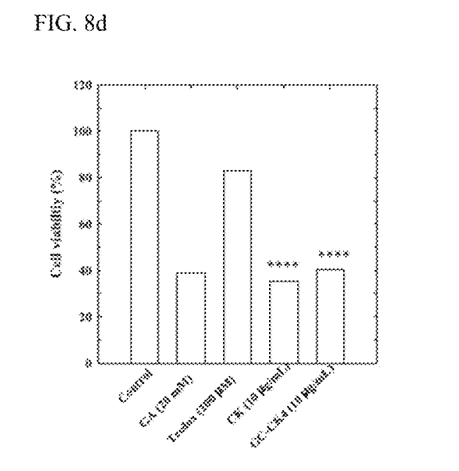
Figure 9A:
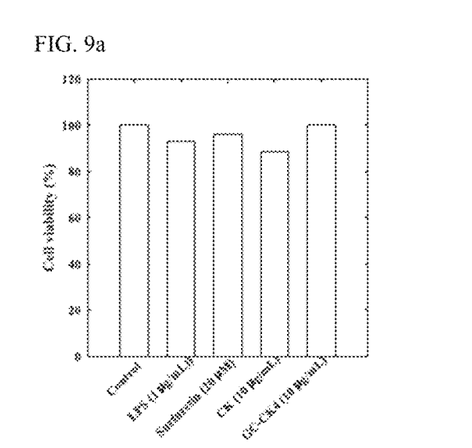
FIGS. 9a and 9b confirm (a) cytotoxicity and (b) inhibition of LPS-induced NO production in RAW264.7 (murine macrophage) cells. The error bar represents standard deviation (n=3) (***P<0.001). Surfuretin (20 μM) was used as a positive control (t-BHP, tert-butyl hydroperoxide; GA, glutamate; LPS, lipopolysaccharide; and NO, nitric oxide).
Figure 9B:
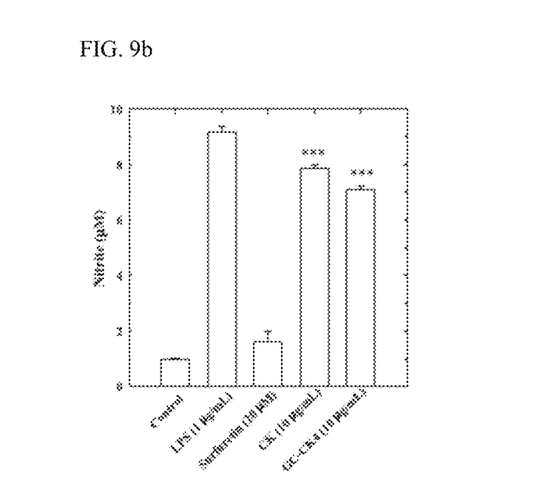

Most of the cells were viable and did not exhibit any cytotoxicity when HT29 cell line was treated with GC (FIG. 8a). From the result above, it was confirmed that GC had biocompatibility. On the contrary, the GC-CK conjugates exhibited similar or higher cytotoxicity in HT29 cells (FIG. 8b), HepG2 cells (FIG. 8c), and HT22 cells (FIG. 8d), compared to CK treatment.

Further, the GC-CK conjugates exhibited lower cytotoxicity when RAW264.7 cells were treated with the GC-CK conjugates compared to CK treatment (FIG. 9a) and inhibited LPS-induced NO production (FIG. 9b). Taken together, it was confirmed that the GC-CK conjugates exhibited cytotoxicity in cancer cells, but not in normal cells (RAW264.7) and inhibited LPS-induced oxidative stress. Therefore, since the GC-CK conjugates have cancer cell-specific apoptotic properties without any side effects, the GC-CK conjugates may be used as targeted anticancer drugs.

Taken together, the GC-CK conjugates of the present invention form spherical nanopariticles in an aqueous solution and has stability for prolonged circulation in the bloodstream. Further, since the GC-CK conjugates have properties for releasing CK at low pH, they can specifically release CK from the cancer tissues, and as a result, they do not exhibit cytotoxicity in normal cells, but exhibit high cytotoxicity in cancer cells. Therefore, the GC-CK conjugates of the present invention, which has high water solubility, may be used as cancer cell-specific anticancer drugs.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents and other embodiments that may be included within the spirit and scope of the present invention as defined by the appended claims.

The invention claimed is:

1. A method for treating colorectal cancer, comprising administering to a patient in need thereof a composition comprising conjugate of carboxylated ginsenoside compound K and glycol chitosan at a concentration of 10 µm/mL, wherein the conjugate comprises an amide bond and an ester linkage in binding sites, and wherein the conjugate releases the ginsenoside compound K at acidic pH.

2. The method according to claim 1, wherein the conjugate forms self-aggregates in an aqueous solution.

3. The method according to claim 1, wherein the conjugate releases the ginsenoside compound K at a pH between 4.0 and 6.0.

4. The method according to claim 1, wherein the conjugate is maintained at least for 8 days without being decomposed at a pH between 7.0 and 8.0.

5. The method according to claim 1, wherein the composition further comprises a pharmaceutically acceptable carrier.

\* \* \* \* \*